United States Patent [19]

Hyeon

[11] Patent Number: 5,116,406
[45] Date of Patent: May 26, 1992

[54] PLANT GROWTH REGULATING COMPOSITION

[75] Inventor: Suong B. Hyeon, Urawa, Japan

[73] Assignee: Mitsubishi Gas Chemical Company, Inc., Tokyo, Japan

[21] Appl. No.: 540,062

[22] Filed: Jun. 19, 1990

[30] Foreign Application Priority Data

Jun. 20, 1989 [JP] Japan .................. 1-155629

[51] Int. Cl.⁵ .................. A01N 41/04; A01N 33/12
[52] U.S. Cl. .................. 71/103; 71/77; 71/92; 71/121; 71/123
[58] Field of Search .................. 71/121, 123, 77, 92, 71/103

[56] References Cited

U.S. PATENT DOCUMENTS

| 4,309,205 | 1/1982 | Kessler ...................... 71/121 |
| 4,337,077 | 1/1982 | Rutherford .................. 71/9 |
| 4,764,201 | 8/1988 | Iino et al. .................. 71/77 |
| 4,799,950 | 1/1989 | Suzuki et al. .................. 71/89 |

FOREIGN PATENT DOCUMENTS

| 61-215305(A) | 3/1985 | Japan . |
| 60-72802(A)  | 4/1985 | Japan . |
| 61-212502(A) | 9/1986 | Japan . |
| 62-190102(A) | 8/1987 | Japan . |
| 2059412A     | 8/1980 | United Kingdom . |

Primary Examiner—Glennon H. Hollrah
Assistant Examiner—John D. Pak
Attorney, Agent, or Firm—Armstrong, Nikaido, Marmelstein, Kubovcik & Murray

[57] ABSTRACT

Disclosed is a plant growth regulating composition, which comprises containing at least one of choline salts and compounds having vitamin $K_3$ activity as active ingredients and a plant growth regulating composition, and comprises containing at least one of choline salt, compounds having vitamin $K_3$ activity and compounds having vitamin $B_1$ activity as active ingredients.

3 Claims, No Drawings

PLANT GROWTH REGULATING COMPOSITION

BACKGROUND OF THE INVENTION

The present invention relates to a plant growth regulating composition.

More particularly, it relates to a plant growth regulating composition for regulating growth of cultivation plants such as cereal crops, vegetables, fruits, flowers, and the like to increase yield of crops and improve quality of the plants.

Hitherto, various studies have been made in attempts to regulate growth of cultivation plants or increase yield and improve quality, but few of them have been put to practical use.

The inventors and others have found that cholines have crop yield increasing effects on sweet potato, onion, Welsh onion, garlic and peach, etc. However, these do not have sufficient crop yield increasing effects to apply practically.

Vitamin $K_3$ is considered to be necessary for biosynthesis of prothrombin which acts on the process of blood coagulation in animals and is known to exist in chloroplast-containing cells of plants. However, with reference to physiological action on plants, very recently it has been found that it has growth promoting effects (for example, in Japanese Patent Kokai (Laid open) Nos. 60-72802 and 61-212502), but these effects are not so high as can be practically applied.

The effect of vitamin $B_1$ on plants has not yet been known.

SUMMARY OF THE INVENTION

The inventors have made pot tests and field tests using at least one of choline salts and at least one of compounds having vitamin $K_3$ activity in combination in an attempt to develop practically safe and effective plant growth regulating compositions and as a result, have found that use of choline salts and vitamins $K_3$ in combination shows much higher regulating activity than that exhibited by the use of them singly.

The inventors have accomplished the present invention based on this finding.

That is, the present invention provides a plant growth regulating composition, which comprises containing at least one of choline salts and at least one of compounds having vitamin $K_3$ activity (hereinafter, is called as vitamins $K_3$) as active ingredients.

Furthermore, the present invention provides a plant growth regulating composition, which comprises at least one of choline salts, vitamins $K_3$ and at least one of compounds having vitamin $B_1$ activity (hereinafter referred to as vitamins $B_1$) as active ingredients.

DETAILED EXPLANATION OF THE INVENTION

In the present invention, choline salts have no special limitation, but typical examples are salts of inorganic acids such as hydrochloride, nitrate, and phosphate of choline and salts of organic acids such as acetate and succinate of choline and practically, hydrochloride of choline (choline chloride) and phosphate of choline are most preferred.

In the present invention, compounds having vitamin $K_3$ activity include menadione and/or menadione sodium hydrogensulfite, menadione dimethylpyrimidinol hydrogensulfite salt, menadoxime, menadiol disulfate salt, menadiol diphosphate salt, menadiol diacetate, and menadiol dibutyrate. The above salts are preferably sodium salts and potassium salts.

Among them, most preferred is menadione sodium hydrogensulfite which is high in water-solubility.

In the present invention, when vitamins $B_1$ are additionally used together with the choline salts and vitamins $K_3$, the plant growth regulating activity further increases.

Vitamins $B_1$ include thiamine hydrochloride salt, thiamine nitrate salt, thiamine phosphate ester, and the like. Among them, hydrochloride or nitrate of thiamine are preferred.

The molar ratio of choline salt and vitamins $K_3$ is 1000:1 to 1000:200, preferably 1000:5 to 1000:100.

When vitamins $B_1$ are added, molar ratio of choline salt, vitamins $K_3$ and vitamins $B_1$ is 1000:1-200:0.1-50, preferably 1000:5-100:0.5-20.

The composition of the present invention is formulated in the form of wettable powder, liquid, emulsifiable concentrate, dust, and granules in the same manner as for conventional plant growth regulating compositions. Furthermore, the composition of the present invention can also be used as a mixture with stabilizer and agricultural agents such as fertilizer components, fungicides, insecticides and the like.

This mixing can be effected either at formulation or at use. The composition of the present invention formulated into wettable powder, liquid and emulsifiable concentrate is diluted with diluents such as water and then is used. Dust and granules are used as they are.

With reference to concentrations of respective components of the composition of the present invention in use, that of choline salt is 1-1500 ppm, preferably 10-1000 ppm in terms of concentration of choline chloride, that of vitamins $K_3$ is 0.1-100 ppm, preferably 0.5-50 ppm in terms of menadione, and that of vitamins $B_1$ is 0-50 ppm, preferably 0.05-30 ppm in terms of thiamine hydrochloride salt.

Method for application of the composition varies depending on kind of plants, but usually any methods of seed immersion, seedling immersion, soil injection, spraying onto leaves, and the like are effective.

Dosage of the composition varies depending on kind of plant, concentration and manner of application and cannot be generically specified, but in case of the above mentioned range of concentration, it is usually 1,000-10,000 1/10a for soil injection and 50-300 1/10a for spraying onto leaves.

The composition of the present invention can be used as a plant growth regulating composition for cereal crops, vegetables and flowers.

EXAMPLES

The present invention will be explained in more detail by the following examples.

EXAMPLE 1

Formulation examples when the composition of the present invention is used as wettable powder or liquid are shown below.

| A. Wettable powder | parts by weight |
|---|---|
| Choline phosphate salt | 10 |
| Menadione | 1 |
| Thiamine hydrochloride salt | 0.3 |
| Sodium dodecylbenzenesulfonate | 2 |
| Polyoxyethylenealkylaryl ether | 1 |

-continued

| A. Wettable powder | parts by weight |
|---|---|
| Talc | 62.7 |
| Bentonite | 23 |

The above materials were uniformly mixed and ground to obtain a wettable powder.

| B. Liquid | parts by weight |
|---|---|
| 75 wt % aqueous choline chloride solution | 20 |
| Menadione sodium hydrogensulfite | 1.7 |
| Thiamine nitrate salt | 0.3 |
| Polyoxyethylenealkyl ether | 1 |
| Water | 77 |

The above materials were uniformly mixed and dissolved to obtain a liquid formulation.

The wettable powder and liquid are diluted with water to a given concentration and is used.

EXAMPLE 2

Base portion of 2–3 cm in length of seedling of sweet potato (var. Kokei No. 14) was immersed in each of aqueous solutions of control compositions and the compositions of the present invention having the liquid composition as shown in Table 1 for 24 hours.

The thus immersed seedling was cultivated in the field and fresh weight of sweet potato roots after a lapse of 120 days from planting of the seedling was measured and the results are shown in Table 1.

One test plot had an area of 3.3 m² and the test was repeated four times. Menadione sodium hydrogen-sulfite was used as vitamins $K_3$ and thiamine hydrochloride salt was used as vitamins $B_1$.

Concentration of menadione sodium hydrogen-sulfite was shown in terms of menadione.

The results are shown in Table 1.

TABLE 1

| No. | Liquid composition | | | Weight of sweet potato Kg/3.3 m² | Ratio to non-treated sweet potato % |
|---|---|---|---|---|---|
| | Choline chloride ppm | VK₃ ppm | VB₁ ppm | | |
| 1 | Non-treated | | | 5.78 | 100 |
| 2 | 0 | 0.9 | 0 | 5.89 | 102 |
| 3 | 0 | 0 | 0.5 | 5.84 | 101 |
| 4 | 0 | 0.9 | 0.5 | 5.90 | 102 |
| 5 | 15 | 0 | 0 | 6.60 | 114 |
| 6 | 21 | 0 | 0 | 6.64 | 115 |
| 7 | 15 | 0 | 0.3 | 6.70 | 116 |
| 8 | 21 | 0 | 0.5 | 6.65 | 115 |
| 9 | 15 | 0.9 | 0 | 8.15 | 141 |
| 10 | 21 | 0.9 | 0 | 7.68 | 133 |
| 11 | 15 | 0.9 | 0.3 | 7.22 | 150 |
| 12 | 15 | 0.9 | 0.5 | 8.96 | 155 |

EXAMPLE 3

Seeds of maize (Delicious) were immersed in each of aqueous solutions of control compositions and the compositions of the present invention which had the liquid composition as shown in Table 2 at 15° C. for 48 hours and washed with water and then dried in the air until the seed surfaces became dry.

These seeds and seeds immersed in water were sown in field soil packed in a plastic pot of 1 liter and raised for 7 days in a greenhouse. Then, the maize seedling was taken out from the pot and roots were washed with water with care not to cut fine roots. Then, the maize was put between filter papers to absorb water into the filter papers and fresh weight was measured.

The results are shown in Table 2.

Menadione sodium hydrogensulfite was used as vitamins $K_3$, thiamine nitrate salt was used as vitamins $B_1$ and choline phosphate salt was used as choline salt.

Concentration of menadione sodium hydrogen-sulfite was shown in terms of menadione in the table.

TABLE 2

| No. | Liquid composition | Weight of portion over the surface of the earth (g/one maize) | Weight of roots (g/one maize) | Weight of roots/ weight of portion over the surface of the earth |
|---|---|---|---|---|
| 1 | Non-treated (immersion in water) | 0.61 | 0.14 | 0.23 |
| 2 | VK₃ 1 ppm | 0.63 | 0.17 | 0.27 |
| 3 | VB₁ 0.5 ppm | 0.62 | 0.16 | 0.26 |
| 4 | VK₃ 1 ppm + VB₁ 0.5 ppm | 0.64 | 0.15 | 0.23 |
| 5 | Choline phosphate salt 30 ppm | 0.74 | 0.20 | 0.27 |
| 6 | Choline phosphate salt 50 ppm | 0.75 | 0.21 | 0.28 |
| 7 | Choline phosphate salt 30 ppm + VK₃ 1 ppm | 1.01 | 0.30 | 0.30 |
| 8 | Choline phosphate salt 50 ppm + VK₃ 1 ppm | 1.03 | 0.30 | 0.29 |
| 9 | Choline phosphate salt 30 ppm + VK₃ 1 ppm + VB₁ 0.5 ppm | 1.06 | 0.31 | 0.29 |
| 10 | Choline phosphate salt 50 ppm + VK₃ 1 ppm + VB₁ 0.5 ppm | 1.13 | 0.33 | 0.29 |

EXAMPLE 4

Each of aqueous solutions of control compositions and the compositions of the present invention which had the liquid composition as shown in Table 3 was sprayed all over peach trees (var. Hakuho, age of tree: 8 years old) 30 days before harvest at a rate of 300 l/10a.

Menadione dimethylpyrimidinol hydrogensulfite was used as vitamins $K_3$ and thiamine nitrate salt was used as vitamins $B_1$.

After harvest, weight of fruit and sugar content were examined and the results are shown in Table 3. Results in the Table were shown by average value of fifty peach fruits of good quality grown in sunny place.

Concentration of menadione dimethylpyrimidinol hydrogen sulfite was shown in terms of menadione.

TABLE 3

| No | Liquid composition | Average weight of fruits (g) | Sugar content (Brix) (%) |
|---|---|---|---|
| 1 | Non-treated | 218.5 | 10.6 |
| 2 | Choline chloride 500 ppm | 230.0 | 10.9 |
| 3 | VK$_3$ 10 ppm | 219.5 | 10.5 |
| 4 | VB$_1$ 1 ppm | 219.0 | 10.6 |
| 5 | VK$_3$ 10 ppm + VB$_2$ 1 ppm | 228.2 | 10.8 |
| 6 | Choline chloride 500 ppm + VK$_3$ 10 ppm | 275.3 | 12.6 |
| 7 | Choline chloride 500 ppm + VK$_3$ 10 ppm + VB$_1$ 1 ppm | 282.3 | 11.7 |

According to the activity of the composition of the present invention, various effects found in choline are synergistically amplified by using vitamins K$_3$ and vitamins B$_1$ in combination with choline and not only amounts of the respective components can be reduced, but also a remarkable growth promoting effect, a germination accelerating effect, a rooting promoting effect, and the like which are not seen by single use of these components are exhibited.

I claim:

1. A plant growth promoting composition, which comprises plant growth promoting effective amounts of choline chloride, and at least one of vitamin K$_3$ compounds selected from the group consisting of menadione sodium hydrogen sulfite, menadione dimethylpyrimidinol hydrogen sulfite, and salts thereof.

2. A plant growth promoting composition according to claim 1, wherein the vitamin K$_3$ compound is menadione sodium hydrogensulfite.

3. A plant growth promoting composition according to claim 1, wherein the molar ratio of choline chloride and the vitamin K$_3$ compound is 1000:1 to 1000:200.

* * * * *